United States Patent [19]

Wunning

[11] Patent Number: 4,485,002

[45] Date of Patent: Nov. 27, 1984

[54] MEASURING DEVICE FOR THE DETERMINATION OF THE ACTIVITY OF CARBON IN FURNACE ATMOSPHERES

[76] Inventor: Joachim Wunning, Bergstrasse 20, 7250 Leonberg-Warmbronn, Fed. Rep. of Germany

[21] Appl. No.: 470,996

[22] Filed: Mar. 1, 1983

[30] Foreign Application Priority Data

Mar. 16, 1982 [DE] Fed. Rep. of Germany ....... 3209438

[51] Int. Cl.³ .......................................... G01N 27/46
[52] U.S. Cl. .................................. 204/424; 204/428; 204/433
[58] Field of Search ............................. 204/421–429, 204/433

[56] References Cited

U.S. PATENT DOCUMENTS

| | | | |
|---|---|---|---|
| 3,403,090 | 9/1968 | Tajiri et al. | 204/1 S |
| 3,546,086 | 12/1970 | Sayles | 204/427 |
| 4,043,890 | 8/1977 | Isaacs et al. | 204/426 |
| 4,088,543 | 5/1978 | Ruka | 204/428 |
| 4,186,072 | 1/1980 | Blumenthal et al. | 204/428 |
| 4,277,322 | 7/1981 | Kane | 204/427 |
| 4,391,690 | 7/1983 | Lin et al. | 204/428 |

Primary Examiner—T. Tung
Attorney, Agent, or Firm—Burns, Doane, Swecker & Mathis

[57] ABSTRACT

A process and apparatus for the determination of the activity of carbon in furnace atmospheres involves the measuring of the ratio of the partial pressure of oxygen in the furnace gas with respect to a reference gas with the aid of an electric potential furnished by oxygen ion conducting solid state cells. The reference gas comprises the furnace gas brought into a Boudouard equilibrium at the furnace temperature. The exchange takes place in a comparison chamber with a time constant 1/10 of that of the furnace. Thus, the activity of carbon may be calculated or calibrated by a formula which includes the electric potential furnished by the solid cells and the absolute temperature, but which does not include the CO content or the pressure. The process may thus be operated without regard for the CO content in the furnace atmosphere.

6 Claims, 3 Drawing Figures

MEASURING DEVICE FOR THE DETERMINATION OF THE ACTIVITY OF CARBON IN FURNACE ATMOSPHERES

BACKGROUND AND OBJECTS OF THE INVENTION

The invention concerns a process and a measuring device for the determination of carbon activity in furnace atmospheres or the like, in which the partial pressure ratio of the oxygen in the furnace gas with respect to a reference gas is determined with the aid of an electric potential supplied by oxygen ion conducting solid state cells.

It is known that in the heat treating of steel in certain cases, particularly in carburizing, the level of carbon (designated C level or C potential) of the furnace atmosphere is measured and regulated. The C level is a single valued function of the activity $a_C$ of carbon, i.e., its vapor pressure ratio with respect to the pure phase (graphite). The afore-mentioned processes are used to determine the activity $a_C$ of furnace atmospheres.

As in the similarly known older processes of dew point and $CO_2$ measurements, the CO content of the furnace atmosphere must be taken into account in the above-mentioned process also, because the oxygen pressure depends on the $P^2_{CO_2}/P^2_{CO}$ ratio, but the $a_C$ activity is a function of the $P^2_{CO}/P_{CO_2}$ ratio. Various methods have been applied to the solution of this problem. Thus, in the so-called carrier gas method a carrier gas with a known CO content is introduced in such volumes, that in case of a varying addition of carburizing gas the CO content of the furnace atmosphere will not be significantly altered.

The disadvantage is a relatively high consumption of energy and gas. It is further known to try to maintain a constant CO content in the furnace by means of a combination of certain alcohols, wherein as a trade-off the disadvantage is accepted that the choice of the carburizing agent is restricted. The CO content in the furnace has been continuously regulated with an additional measuring instrument and the C level corrected accordingly. The disadvantage of such a process is the high cost of investment and maintenance.

It is therefore the object of the present invention to provide a process of the afore-mentioned type whereby without the additional consumption of energy, with simple means the determination of the activity of carbon becomes possible. Simultaneously, a suitable measuring cell is provided whereby this object may be attained.

SUMMARY OF THE INVENTION

The invention initially involves a process of the above-described type wherein the reference gas comprises the furnace gas as brought into Boudouard equilibrium[x] with carbon at the furnace temperature. This process has the advantage that the activity of the carbon may be calculated or calibrated by means of a formula which contains the electric potential supplied by solid state cells and the absolute temperature, but not the CO content and the pressure. The new process is thus capable of working in the furnace atmosphere with consideration of the CO content, thereby avoiding the disadvantages of the known measuring methods.

[x] Boudouard equilibrium is the name for the equilibrium reaction $2CO \rightleftharpoons C + CO_2$.

To practice the new process, preferably a measuring installation is used which is equipped with two measuring chambers separated by the oxygen ion conducting solid electrolyte material, with at least one electrode being assigned to each chamber, as is done in the known measuring methods. The novel feature involves the fact that a measuring cell is provided that is filled with carbon and connected through an orifice with the furnace atmosphere or a measuring chamber which in turn is exposed to the furnace atmosphere. In a simple manner, the measuring cell comprises an electrolyte tube closed on one side and obturated on the open side by a stopper with the connecting orifices to the furnace atmosphere. The electrodes are mounted on this electrolyte tube on the closed side, inside and outside. This configuration is compact, can be made significantly shorter, and is not exposed to compression forces, i.e., it has the same pressure both inside and outside It is therefore substantially less likely to fracture than the measuring tubes of known configuration.

The outer electrode may be contained in a protective pipe surrounding the electrolyte tube, which pipe additionally may be equipped with orifices for the access of furnace gases or with a connection for the forced introduction of furnace gas. A structurally simple configuration is obtained when the magnitude of the connecting orifices in the stopper of the electrolyte tube is chosen so that the time constant determined by the diffusion of the furnace gas may be obtained in the above-described sense. If the measuring cell is surrounded by the protective pipe, a measuring chamber may be formed within the protective pipe, which may be provided with an additional orifice for the introduction of a test gas for calibrating purposes. The measuring device designed in this manner, permits the execution of the new process in a simple manner.

THE DRAWING

The drawing shows a preferred embodiment of a new measuring installation for the process according to the invention, together with its behavior over a period of time. In the drawing.

DETAILED DESCRIPTION OF A PREFERRED EMBODIMENT OF THE INVENTION

Figure 1:
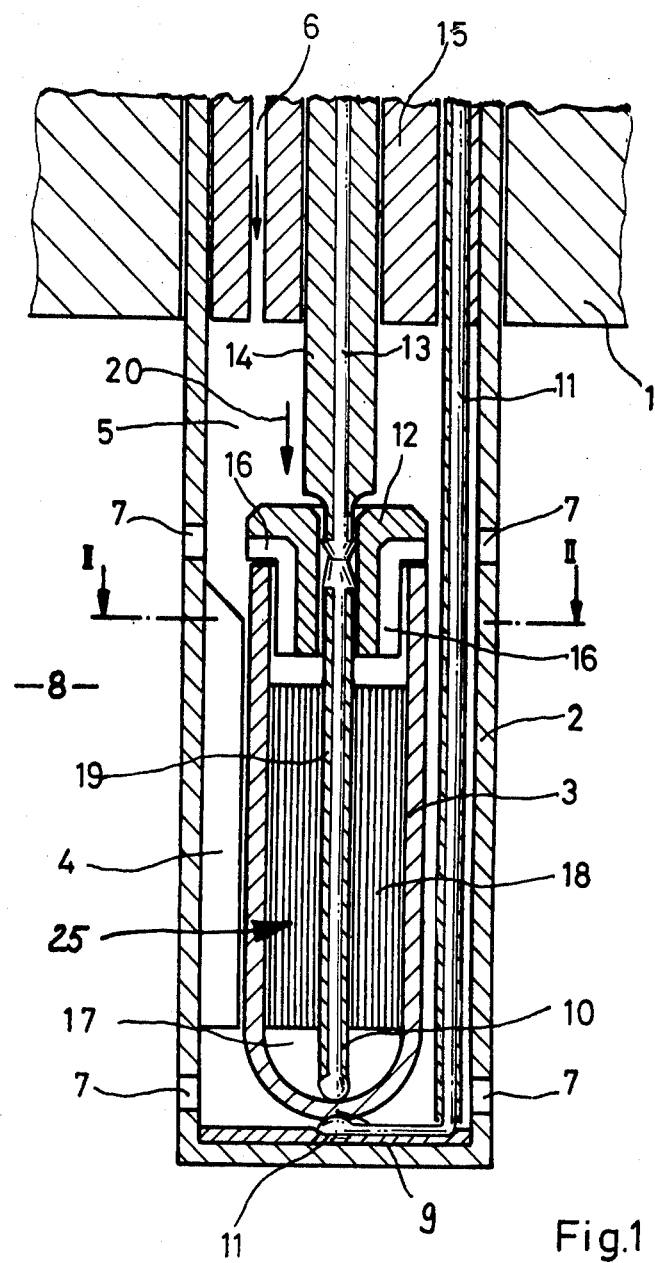
FIG. 1 shows a schematic longitudinal section through a new measuring installation comprising a measuring cell and a protective pipe surrounding said measuring cell, together with an electrode arrangement.
Figure 2:
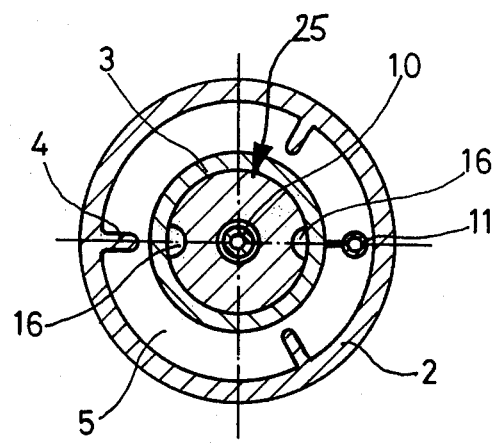
FIG. 2 is a section through the measuring installation of FIG. 1 on the line II—II.

FIG. 1 shows schematically a protective pipe 2 penetrating through the furnace wall 1 and surrounding a measuring cell 25. The latter is held by means of three radial ribs 4 of the pipe distributed uniformly around the circumference, in an approximately concentric manner. Inside the protective pipe 2, a measuring chamber 5 is formed, which is connected either forcibly by means of an inlet orifice 6 from outside the furnace or through the orifices 7 with the furnace atmosphere present in the furnace space 8 surrounding the protective pipe 2. That is, the orifice 6 is only used as an alternative to the orifice 7, e.g., when the device is being calibrated, or in case of a burn-out of the furnace as will be explained hereinafter. The measuring cell 25 comprises an electrolyte tube 3 closed on one end and containing a carbon filling 18. A stopper 12 closes the other end of the tube 3 and has connecting orifices 16 communicating with the furnace atmosphere. An inner electrode 10 is disposed within the tube 3.

At the lower, closed end 9 of the tube 3, the inner electrode 10 is in contact with the tube. Outside of the tube is disposed an electrode 11, which extends upwardly in the area of the edge of the protective pipe 2. The inner electrode part 10 extends centrally in the electrolyte tube 3 upwardly into the center orifice of the stopper 12 and is there connected with an inlet line 13, which outside the furnace is used to measure the difference in potential of the electrodes 10 and 11. The inlet line 13 is located in a pipe 14, which in turn, is passed through a mounting 15 with the latter also containing the inlet orifice 6.

The stopper 12 has, in the preferred embodiment, two diametrically opposed connecting orifices 16, which effect the connection of a comparison chamber 17 in the electrolyte tube 3 with the measuring chamber 5 and the atmosphere of the furnace. The carbon filling 18 is located in the comparison chamber 17 and preferably comprises active charcoal with a typical bulk density of 0.5 g/cm and a surface of 700 m$^2$/g. A catalyst, for example fineley distributed iron, may be applied further, to facilitate the desired establishment of the Boudouard equilibrium. The inner electrode 10 is located in a ceramic support pipe 19, which serves to transmit the spring force applied by the pipe 14 in the direction of the arrow 20 to press against the electrode 10.

In the preferred embodiment, the introduction of the furnace gas from the furnace space 8 into the measuring chamber 5 is normally effected through the orifices 7, the dimensions of which are chosen so that a nearly uninhibited exchange of gas with the furnace space 8 is possible. The time constant is therefore chosen to be less than a second. The orifices 16 are designed so that the time constant for the exchange of gas between the measuring chamber 5 and the comparison chamber 17, effected by diffusion, yields a time constant of 1/10 of that for the exchange of gas between the furnace atmosphere and the adjacent measuring chamber 5. For calibration purposes, the measuring chamber 5 may be filled with a calibration gas through the connection 6, which may further be used to prevent the increased consumption of carbon in the comparison chamber 17 in case of a burn-out of the furnace. This is obtained by the automatic introduction of inert gas, for example, if the activity of the carbon is declining below a certain predetermined limiting value, such as 0.2.

It is obviously also possible to employ other measuring cell configurations in an analogous manner, for example, a chamber equipped with an electrode plate and the electrode and filled with carbon. However, an electrolyte tube closed on one side, as proposed hereinabove, is simpler in its application to the measuring cell 25 and is better in view of the diffusion flow conditions.

It is important in the new process to effect the exchange of gas in the comparison installation within a period of time sufficiently long to attain the Boudouard equilibrium, but not to allow the consumption of carbon to become excessive in view of the life of the measuring cell used, while transmitting the fluctuations in time of the CO content of the furnace with the least possible attenuation, so as to keep the measuring error low. It has been found to be advantageous to effect the exchange of gas in the comparison installation with a time constant of the order of magnitude of 1/10 of the furnace, so that a period of time between 20 and 100 seconds will yield the most favorable values for the measurement. This is based on the following considerations.

The exchange of gas in the measuring cell is characterized by the time constant $k=V/G$ ($V=$volume, $G=$gas flow). This time constant must satisfy certain requirements which are partially contradictory, such as:

1. The Boudouard equilibrium must be nearly completely established in the comparison installation ($a_c>0.99$) to avoid measuring errors. This requires a large time constant.

2. As the activity of carburizing atmospheres is usually less than 1, the carbon is consumed in the measuring cell with increasing rapidity with rising gas exchanges. Here again, the longest possible time constant is needed.

3. In order to be able to transmit the fluctuations in time of the CO content in the furnace with the slightest possible attenuation to the comparison arrangement, a short time constant is needed.

These three requirements are satisfied in an advantageous manner, if the time constant for the exchange of gas in the comparison installation, as mentioned hereinabove, amounts to approximately 1/10 of the change of gas in the furnace. It has been discovered that the time constant of the CO variations in carburizing furnaces in accordance with the laws of flushing is higher by approximately two orders of magnitude than that of the value measured itself (oxygen), which is a function of the velocity of chemical reactions. The change of gas in the comparison installation may be attenuated correspondingly.

As under industrial conditions, the time constant of the variation of the CO in carburizing installations as a rule is between 200 and 1000 seconds, the time constant of the measuring cell itself should amount to approximately 20 to 100 seconds. It was found that the Boudouard equilibrium desired is thereby established without the overly rapid consumption of the carbon charge in the comparison installation. The carbon charge is consumed by half after approximately $10^6$ time constants, so that even in continuous operation, lives of more than one year may be obtained.

The effect of temperature in the measured result is slight. The activity of carbon is calculated by the formula: $a_C=\exp(-23.3 \times E/T)$. Herein, E is the cell potential in mV, T the absolute temperature in K. It is seen that the effect of temperature is less than in the conventional measuring processes. In the case of furnace atmospheres with an activity $a_C>0.9$, such as those occurring for example during carburizing in the first process phase and in the neutral annealing of high carbon steels, temperature compensation may be entirely omitted. Temperature compensation may be effected in all other cases with the by means of the furnace measuring installation which is present in any case.

The mode of operation of the new measuring installation shall now be explained in detail. During a measuring phase, the gas inside the comparison chamber 17 will be at the Boudouard equilibrium, while outside the chamber 17 in the measuring chamber 5, the carbon content will be less, i.e., it will correspond to the carbon content of the furnace gas. Thus, there will occur a difference of partial pressure ratio between the chamber 17, 5, creating a difference of electrical potential which is measured by the electrodes.

In Table I for this purpose, measured values for four furnace atmospheres with different CO contents or pressures are compared for a C level of 0.75% and a temperature of 920° C. Only the measuring signal of the activity cell is of the same magnitude for all of the atmospheres.

it is not necessary to take the partial pressure of the CO content in the furnace.

Although the present invention has been described in connection with a preferred embodiment thereof, it will be appreciated by those skilled in the art that additions, deletions, substitutions, and modifications may be made without departing from the spirit and scope of the invention as defined in the appended claims.

TABLE I

| Temperature | T = 1193 K (920° C.) | | | | |
|---|---|---|---|---|---|
| Activity | $a_C = 0.50$ | Furnace Atmosphere No. | | | |
| C level | $C_p = 0.75\%$ C | 1 | 2 | 3 | 4 |
| Furnace Atmosphere Pressure, bar | | 1.0 | 1.0 | 1.0 | 0.1 |
| (rest $N_2$) | CO, volume % | 20.0 | 15.0 | 2.0 | 2.0 |
| | $H_2$, volume % | 40.0 | 35.0 | 2.0 | 2.0 |
| Conventional | $CO_2$, volume % | 0.164 | 0.092 | $1.6 \times 10^{-3}$ | $1.6 \times 10^{-4}$ |
| measure | Dew point, °C. | −4.2 | −9.0 | −55.0 | −71.0 |
| values | $E_{air}$, mV | 1127.0 | 1142.0 | 1245.0 | 1304.0 |
| (state of the art) | | | | | |
| Activity cell, | $E_{akt}$, mV | 35.5 | 35.5 | 35.5 | 35.5 |

Figure 3:
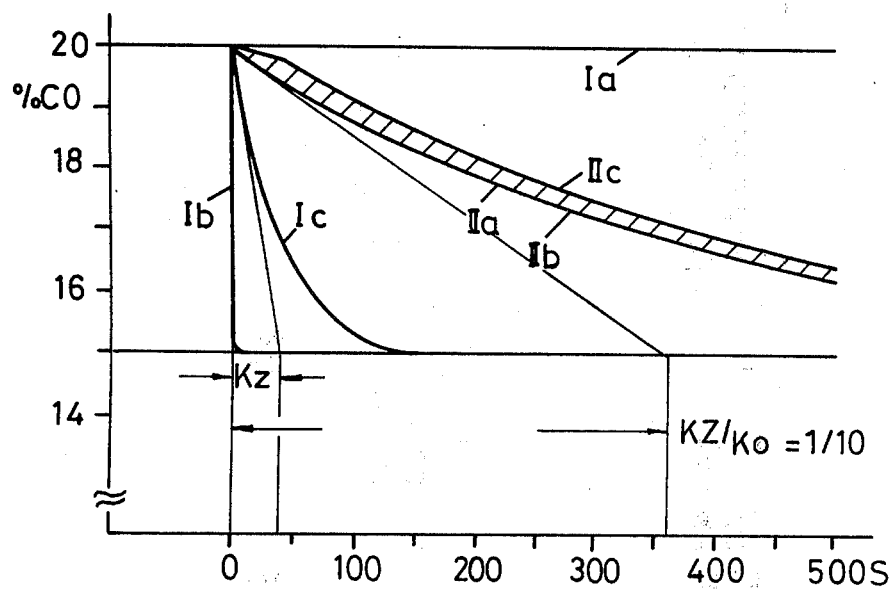
FIG. 3 is a graphic representation of the behavior in time of the concentration variation of CO in the furnace and as a function of it, in the measuring installation.

The new measuring installation may be designed so that the behavior in time shown in FIG. 3 by a time diagram is obtained. Conditions for this behavior are compiled in Table II.

TABLE II

| | Volume in $cm^3$ | Gas Supplied or Exchanged in $cm^3/s$ (920° C.) | | Time Constant in s (920° C.) |
|---|---|---|---|---|
| (a) Furnace | $2 \times 10^6$ | gas introduced | 5555.0 | 360.0 |
| (b) Measuring chamber | 10 | test gas | 5.55 | 1.8 |
| (c) Cell | 1 | measuring chamber gas | 0.028 | 36.0 |

Let the chamber 8, 5 and 17 be initially filled with atmosphere No. 1 (see Table I) with a gas containing 20% CO.

CASE I—The measuring chamber 5 is flushed with the test gas (atmosphere No. 2), with the CO gas behaving, due to the short time constant, practically in accordance with a step function (Ib). From the transfer function of the measuring cell 25 (Ic), its time constant may be read and the function tested. The furnace temperature remains practically constant (Ia).

CASE II—The supply of gas to the furnace is switched to atmosphere No. 2. The time behavior of the CO content in the furnace 8 and the measuring chamber 5 are practically identical (IIa and IIb), while the measuring cell 25 follows a slight delay (IIc). The error caused by the differential CO content (shaded) in the activity $a_C$ may be tolerated (>3%).

The atmosphere step according to Case II may occur in the carburizing process, when a mixture of alcohol and nitrogen is used and in the course of the process the alcohol component is reduced. With the new measuring

What is claimed is:

1. A measuring device for determining the activity of carbon in an atmosphere comprising means forming first and second chambers separated by an oxygen ion conducting solid electrolyte, first and second electrodes arranged in communication with said first and second chambers, respectively, one of said chambers defining a comparison chamber and the other defining a measuring chamber, a first orifice for communcating said measuring chamber with an atmosphere, said comparison chamber containing a carbon supply, and a second orifice communicating said comparison chamber with said measuring chamber.

2. Measuring device according to claim 1, wherein said comparison chamber is arranged in an electrolyte tube closed at one end, a stopper closing said electrolyte tube on the open side and having said second orifice.

3. Measuring device according to claim 2, wherein said first electrode communicates with said comparison chamber and extends centrally through the carbon within a ceramic supporting pipe.

4. Measuring device according to claim 3, wherein said stopper has a center orifice for the passage of said first electrode and said ceramic pipe.

5. Measuring device according to claim 3, wherein said comparison chamber is defined by an electrolyte tube, a protective pipe surrounding said tube and containing said second electrode.

6. Measuring device according to claim 5, characterized in that said measuring chamber is defined by said protective pipe and contains said first orifice.

* * * * *